(12) United States Patent
Herrmann et al.

(10) Patent No.: US 7,931,932 B2
(45) Date of Patent: Apr. 26, 2011

(54) PROCESSES FOR PRODUCING POLYMER COATINGS THROUGH SURFACE POLYMERIZATION

(75) Inventors: Robert A. Herrmann, Boston, MA (US); Frederick H. Strickler, Natick, MA (US); Wendy Naimark, Boston, MA (US); Peter L. Dayton, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/070,275

(22) Filed: Feb. 14, 2008

(65) Prior Publication Data

US 2008/0145516 A1 Jun. 19, 2008

Related U.S. Application Data

(63) Continuation of application No. 10/116,647, filed on Apr. 4, 2002, now abandoned.

(51) Int. Cl.
*B05D 3/06* (2006.01)
*C08F 2/46* (2006.01)
*C08F 295/00* (2006.01)
*A61F 2/06* (2006.01)

(52) U.S. Cl. .... 427/2.1; 427/2.24; 427/2.25; 427/372.2; 623/1.11; 623/1.42; 424/425; 525/269

(58) Field of Classification Search .................. 427/2.1, 427/2.24, 2.25, 487; 623/1.11, 1.42; 424/425; 525/269
See application file for complete search history.

(56) References Cited

U.S. PATENT DOCUMENTS

| | | | |
|---|---|---|---|
| 4,486,574 A | 12/1984 | Murray | 525/333.4 |
| 4,946,899 A | 8/1990 | Kennedy et al. | 525/344 |
| 5,118,424 A | 6/1992 | MacRae | 210/653 |
| 5,376,400 A | 12/1994 | Goldberg et al. | 427/2.24 |
| 5,700,286 A | 12/1997 | Tartaglia et al. | 623/1 |
| 5,733,925 A | 3/1998 | Kunz et al. | 514/449 |
| 5,735,897 A | 4/1998 | Buirge | 623/12 |
| 5,741,331 A | 4/1998 | Pinchuk | 623/11 |
| 5,749,968 A | 5/1998 | Melanson et al. | 118/300 |
| 5,800,373 A | 9/1998 | Melanson et al. | 602/82 |
| 5,807,937 A * | 9/1998 | Matyjaszewski et al. | 526/135 |
| 5,837,313 A | 11/1998 | Ding et al. | 427/2.21 |
| 5,844,016 A | 12/1998 | Sawhney et al. | 522/13 |
| 5,866,113 A * | 2/1999 | Hendriks et al. | 424/78.17 |
| 5,900,245 A | 5/1999 | Sawhney et al. | 424/426 |
| 6,051,248 A | 4/2000 | Sawhney et al. | 424/426 |
| 6,120,904 A | 9/2000 | Hotettler et al. | 428/423.3 |
| 6,121,341 A | 9/2000 | Sawhney et al. | 522/84 |
| 6,179,817 B1 | 1/2001 | Zhong | 604/265 |
| 6,197,051 B1 | 3/2001 | Zhong | 623/1.46 |
| 6,217,894 B1 | 4/2001 | Sawhney et al. | 424/426 |
| 6,231,600 B1 | 5/2001 | Zhong | 623/1.42 |
| 6,310,165 B1 * | 10/2001 | Wang | 526/348 |
| 6,319,990 B1 | 11/2001 | Spence et al. | 525/209 |
| 6,323,304 B1 | 11/2001 | Lemmon et al. | 528/286 |
| 6,326,420 B1 | 12/2001 | Olson et al. | 523/334 |
| 6,387,379 B1 | 5/2002 | Goldberg et al. | 424/400 |
| 6,391,391 B2 * | 5/2002 | Barkac et al. | 427/386 |
| 6,545,097 B2 * | 4/2003 | Pinchuk et al. | 525/240 |
| 6,599,558 B1 * | 7/2003 | Al-Lamee et al. | 427/2.24 |
| 6,669,980 B2 * | 12/2003 | Hansen | 427/2.24 |
| 6,673,385 B1 | 1/2004 | Ding et al. | 427/2.28 |
| 7,056,983 B2 * | 6/2006 | Nakagawa et al. | 525/242 |
| 2001/0014717 A1 | 8/2001 | Hossainy et al. | 525/60 |
| 2003/0134032 A1 * | 7/2003 | Chaouk et al. | 427/2.24 |
| 2004/0144655 A1 * | 7/2004 | Bertrand et al. | 205/235 |
| 2006/0009550 A1 * | 1/2006 | Messersmith et al. | 524/17 |

FOREIGN PATENT DOCUMENTS

| | | |
|---|---|---|
| WO | WO 00/59963 | 10/2000 |
| WO | WO 01/17575 | 3/2001 |
| WO | WO 02/058753 | 8/2002 |
| WO | WO 02/070022 | 9/2002 |

OTHER PUBLICATIONS

Hester et al. ATRP of Amphiphilic graft copolymers bond on pVDF and their use as membrane additives. Macromolecules. 2002. vol. 35 pp. 7652-7661.*

* cited by examiner

*Primary Examiner* — Timothy H Meeks
*Assistant Examiner* — Cachet I Sellman
(74) *Attorney, Agent, or Firm* — Mayer & William PC; David B. Bonham; Keum J. Park

(57) ABSTRACT

A medical device with a therapeutic agent-releasing polymer coating. The medical device is provided by a method that comprises: (a) attaching at least one reactive species to a medical device surface, which reactive species leads to chain growth polymerization in the presence of monomer; (b) contacting the reactive species with at least one monomer species, thereby forming a polymer coating on the surface of the medical device; and (c) providing at least one therapeutic agent within the polymer coating. The therapeutic agent may be incorporated during formation of the polymer coating or after formation of the polymer coating. The at least one reactive species can comprise, for example, a free radical species, a carbanion species, a carbocation species, a Ziegler-Natta polymerization complex, a metallocene complex, and/or an atom transfer radical polymerization initiator. Alternatively, the medical device is provided by a process comprising: (a) immobilizing least one polymerization catalyst at a medical device surface, which polymerization catalyst leads to polymerization in the presence of monomer; (b) contacting the medical device surface with at least one monomer species, thereby forming a polymer coating at the surface of the medical device; and (c) providing at least one therapeutic agent within the polymer coating.

18 Claims, No Drawings

PROCESSES FOR PRODUCING POLYMER COATINGS THROUGH SURFACE POLYMERIZATION

STATEMENT OF RELATED APPLICATION

This is a continuation of U.S. patent application Ser. No. 10/116,647, filed Apr. 4, 2002, now abandoned, entitled "Processes for Producing Polymer Coatings Through Surface Polymerization," which is incorporated herein by reference in its entirety.

BACKGROUND OF THE INVENTION

1. Field of the Invention

The present invention relates to medical devices with polymeric coatings and more particularly to medical devices having polymer coatings that release therapeutic agent.

2. Brief Description of the Background Art

Local delivery of therapeutic agents is an important adjunct to mechanical treatment of diseases. For example, local delivery of restenosis-inhibiting therapeutic agents has been proposed in connection with the insertion of a coronary stent after percutaneous transluminal coronary angioplasty, as the presence of the stent can exacerbate neointimal hyperplasia, which is believed to be a significant causative factor in the restenosis of the vessel.

One common method of local therapeutic agent delivery is to allow the therapeutic agent to diffuse from a polymer matrix. In this connection, controlling release is an important aspect in providing effective therapy. Furthermore, controlling the manufacture of the polymer matrix is an important factor in determining the ultimate release rate.

SUMMARY OF THE INVENTION

The present invention provides a method of producing a polymer on a medical device in which polymer chains are grown at the surface of the medical device to provide a polymer coating.

According to one aspect of the presenting invention, a medical device with a therapeutic agent-releasing polymer coating is provided by a method that comprises: (a) attaching at least one reactive species to a medical device surface, which reactive species leads to chain growth polymerization in the presence of monomer; (b) contacting the reactive species with at least one monomer species, thereby forming a polymer coating on the surface of the medical device; and (c) providing at least one therapeutic agent within the polymer coating.

The therapeutic agent may be incorporated during formation of the polymer coating or after formation of the polymer coating.

In certain embodiments, the reactive species is formed from a derivatized monomer that is covalently bonded to the surface of the medical device.

In certain other embodiments, the reactive species is formed from a derivatized initiator compound that is covalently bonded to the surface of the medical device.

The reactive species can comprise, for example, a free radical species, a carbanion species, a carbocation species, a Ziegler-Natta polymerization complex, a metallocene complex, and/or an atom transfer radical polymerization initiator.

Where a free radical species is used, it can be provided, for example, by a process comprising (a) covalently attaching a free-radical initiator molecule to the surface or (b) covalently attaching a species that acquires a free-radical upon exposure to a free radical initiator molecule.

Where a carbanion species is used, it can be provided, for example, by a process comprising (a) covalently attaching an anionic initiator molecule to the surface or (b) covalently attaching a species that acquires a carbanion upon exposure to an anionic initiator molecule.

Where a carbocation species used, it can be provided, for example, by a process comprising covalently attaching a species that develops a carbocation upon exposure to a cationic initiator molecule.

Where atom transfer radical polymerization is used the at least one reactive species can be provided, for example, by a process comprising: (a) covalently attaching an atom transfer radical polymerization initiator molecule to the surface or (b) covalently attaching a species that acquires a free-radical upon exposure to an atom transfer radical polymerization initiator and an atom transfer radical polymerization catalyst.

According to another aspect of the present invention, a medical device with a therapeutic agent-releasing coating is provided by a process comprising: (a) immobilizing least one polymerization catalyst at a medical device surface, which polymerization catalyst leads to polymerization in the presence of monomer; (b) contacting the medical device surface with at least one monomer species, thereby forming a polymer coating at the surface of the medical device; and (c) providing at least one therapeutic agent within the polymer coating.

One advantage of the present invention is that a process is provided that allows for controlled manufacture of drug delivery polymer coatings on medical device surfaces.

Another advantage of the present invention is that a process is provided, which allows many medical devices to be coated at the same time, improving manufacturing efficiency and cost effectiveness.

The above and other embodiments and advantages of the present invention will be readily understood by those of ordinary skill in the art upon review of the Detailed Description and Claims to follow.

DETAILED DESCRIPTION OF THE INVENTION

Methods for providing medical devices having therapeutic-agent-releasing polymer coatings are provided below in accordance with various embodiments of the invention.

Preferred medical devices for use in conjunction with the present invention are implantable or insertable medical devices, including catheters (for example, urinary catheters or vascular catheters), guide wires, balloons, filters (e.g., vena cava filters), stents (including coronary vascular stents, cerebral, urethral, ureteral, biliary, tracheal, gastrointestinal and esophageal stents), stent grafts, cerebral aneurysm filler coils (including GDC—Guglilmi detachable coils—and metal coils), vascular grafts, myocardial plugs, patches, pacemakers and pacemaker leads, heart valves, biopsy devices or any polymer coated substrate (which can be, for example, metallic, polymeric or ceramic) for use in the human body, either for procedural use or as an implant.

The medical devices contemplated for use in connection with the present invention include drug delivery medical devices that are used for either systemic treatment or for the treatment of any mammalian tissue or organ. Non-limiting examples of tissues and organs include the heart, coronary or peripheral vascular system, lungs, trachea, esophagus, brain, liver, kidney, bladder, urethra and ureters, eye, intestines, stomach, pancreas, ovary, and prostate; skeletal muscle; smooth muscle; breast; cartilage; and bone.

Medical devices made in accordance with the present invention can be placed in a wide variety of bodily locations for contact with bodily tissue and/or fluid. Some preferred placement locations include the coronary vasculature or peripheral vascular system (referred to collectively herein as "the vasculature"), gastrointestinal tract, esophagus, trachea, colon, biliary tract, urinary tract, prostate and brain.

In some embodiments of the present invention, a polymer coating is provided by first attaching one or more reactive species to at least a portion of the surface of a medical device. Subsequent contact with a monomer-containing liquid leads to chain-growth polymerization at the site of the attached species. In this manner, a polymer coating is produced that is attached to the surface of the medical device.

A "monomer" is a polymerizable molecule. For example, monomers may be small molecules, such as those listed below; or they may be larger molecules containing polymerizable groups, for example, polymers containing >C=C< groups. A "polymer" is composed of two or more monomers, and includes dimers, trimers, tetramers, etc.

Preferred monomers for embodiments of the invention that utilize chain-growth polymerization (e.g., addition polymerization) are unsaturated monomers, including, for example: (a) alkylene monomers and derivatives, such as ethylene, propylene, butylenes (e.g., isobutylene), and fluorinated alkylene monomers (e.g., tetrafluoroethylene); (b) vinyl monomers and derivatives, such as styrene, vinyl chloride, vinyl pyrrolidone, acrylonitrile, vinyl alcohol, and vinyl acetate; and (d) acrylic acid monomers and derivatives, such as methyl acrylate, methyl methacrylate, acrylic acid, methacrylic acid, acrylamide, hydroxyethyl acrylate, hydroxyethyl methacrylate, glyceryl acrylate, glyceryl methacrylate, methacrylamide and ethacrylamide.

Polymerization can proceed via essentially any known chain-growth polymerization mechanism, including free-radical polymerization, cationic polymerization, anionic polymerization, Ziegler-Natta polymerization, metallocene polymerization, and atom transfer radical polymerization.

In some chain-growth polymerization reactions, including several of the reactions discussed below, an initiator molecule becomes incorporated into the polymer that is formed. In some cases, the initiator molecule is attached to the medical device surface. A polymer is then formed by exposing the attached initiator to monomer, along with any desired auxiliary species (e.g., co-initiators, catalysts, co-catalysts, electron donors, accelerators, sensitizers, etc.) under any desired reaction conditions (for example, irradiation and/or heat). Examples of initiators include free radical initiators, anionic initiators, cationic co-initiators and atom transfer radical polymerization initiators. For example, the medical device can be formed from a material that provides chemically reactive groups or the surface of the medical device can be treated with a reagent that places chemically reactive groups on the device surface or with a coating that supplies such groups. These groups are then reacted with groups that are either inherently found on the initiator molecule or are supplied to the initiator molecule (i.e., a derivatized form of the initiator is used). Covalent attachment may be carried out using numerous known reaction chemistries.

In other embodiments of the invention, a transformable molecule is attached to the medical device surface, which is transformed into a reactive species upon interaction with an initiator or catalyst molecule. The chain growth occurs at the site of the reactive species upon exposure to an appropriate monomer under the appropriate conditions.

The transformable molecule is typically an unsaturated molecule, and more typically a monomer that is derivatized for attachment to the device surface.

To avoid the initiation of polymer chains not attached to the surface, it is preferred, for example, to either (a) limit the quantity of initiator or catalyst added or (b) remove excess initiator or catalyst before the introduction of monomer.

As with the initiator molecule, attachment of the transformable molecule can be covalent. For example, in the case where the transformable molecule is a monomer, attachment typically occurs through groups that are either inherently found on the monomer or are supplied to the monomer (e.g., a derivatized form of the monomer is used).

Specific examples include the following: (a) interaction between an attached unsaturated molecule and a free-radical initiator can be used to generate an attached free radical species, which leads to chain growth in the presence of monomer, (b) interaction between an attached unsaturated molecule and a cationic initiator can be used to generate an attached carbocationic species, which leads to chain growth in the presence of monomer, (c) interaction between an attached unsaturated molecule and an anionic initiator can be used to generate an attached carbanion species, which leads to chain growth in the presence of monomer, (d) interaction between an attached unsaturated molecule and a Ziegler-Natta catalyst/co-catalyst system can be used to generate an attached reactive species, which leads to chain growth in the presence of monomer, (e) interaction between an attached unsaturated molecule and a metallocene catalyst can be used to generate an attached reactive species, which leads to chain growth in the presence of monomer, and (f) interaction between an attached unsaturated molecule and an atom transfer radical polymerization initiator system can be used to generate an attached reactive species, which leads to chain growth in the presence of monomer.

Suitable free radical initiator compounds for use in connection with free-radical polymerization embodiments of the present invention include hydroperoxide, peroxide, di-tert-butyl peroxide, di-benzoyl peroxide, and azo compounds, such as azobis(isobutyronitrile), tertiary butyl perbenzoate, di-cumyl peroxide and potassium persulfate.

According to a specific exemplary embodiment of the invention, a substrate surface is provided, which contains free hydroxyl groups. Subsequently a molecule including a vinyl group is covalently bonded to the surface. For example, vinyl-trimethoxysilane can be reacted with the —OH groups on the surface, leaving a vinyl group attached to the surface for subsequent polymerization (e.g., free-radical polymerization) with a number of monomeric species.

According to another a specific exemplary embodiment of the invention, a free radical polymerization of methyl methacrylate is conducted to provide a polymeric coating on the surface of a medical device. Initially, a methyl methacrylate derivative is covalently attached to the medical device surface

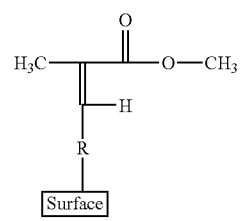

as shown, where R is an organic radical, typically a hydrocarbon chain. A free radical initiator such as a peroxide compound is added, generating a free radical species within the attached molecule. Subsequently, methyl methacrylate monomer is added to commence chain growth polymerization, which proceeds from the attached molecule. The result is a medical device with a covalently attached polymethylmethacrylate coating. Where R is an initiator molecule attached to the surface, polymerization would occur through the illustrated double bond.

In related embodiments, the attachment of the methacrylate derivative can occur through the ester group. For example, a functionalized methacrylate, such as glycidyl methacrylate, hydroxy ethyl methacrylate, methacrylic acid, can initially be attached to the surface. The initiator then generates the free-radicals, and methyl methacrylate monomer is added to start polymer formation.

Metallocene catalysts are coordination compounds that are cyclopentadienyl derivatives of metal-containing ions (e.g., transition metal ions or transition metal halide ions). Examples of metallocene catalysts for use in metallocene polymerization embodiments of the present invention include ferrocene and bis-chlorozirconocene. Their use in the polymerization of unsaturated monomers is well known.

Ziegler-Natta catalysts are also well known. Typical Ziegler-Natta catalysts for use in Ziegler-Natta polymerization embodiments of the present invention include a transition metal compound, for example, titanium halides such as $TiCl_3$ or $TiCl_4$, in combination with an organo aluminum compound, for example, a trialkyl aluminum or dialkylaluminum halide such as $Al(CH_2H_5)_2Cl$ or $Al(C_2H_5)_3$. An electron donor is also typically included.

In an atom transfer radical polymerization process, one or more radically polymerizable monomers are polymerized in the presence of an initiator and a catalyst, which includes a transition metal complexed by one or more ligands. The transition metal is any transition metal compound that can participate in a redox cycle with the initiator and the growing polymer chain. Transition metal catalysts include those represented by the following general formula $TM^{n+}X_n$, where TM is the transition metal, n is the formal charge on the transition metal having a value of from 0 to 7, and X is a counterion or covalently bonded component. Examples of the transition metal (TM) include, but are not limited to, Cu, Fe, Au, Ag, Hg, Pd, Pt, Co, Mn, Ru, Mo, Nb and Zn. Examples of X include, but are not limited to, halide, hydroxy, oxygen, $C_1$-$C_6$ alkoxy, cyano, cyanato, thiocyanato and azido. A preferred transition metal is Cu(I) and X is preferably halide. Ligands include compounds having one or more nitrogen, oxygen, phosphorus and/or sulfur atoms, which can coordinate to the transition metal catalyst compound, such as unsubstituted and substituted pyridines and bipyridines; porphyrins; cryptands; crown ethers; polyamines; alkylene glycols; carbon monoxide; as well as coordinating monomers, for example, styrene, acrylonitrile and hydroxyalkyl (meth)acrylates. Initiators that may be used include organic compounds, such as aliphatic compounds, cycloaliphatic compounds, aromatic compounds, polycyclic aromatic compounds, heterocyclic compounds, sulfonyl compounds, sulfenyl compounds, esters of carboxylic acids, nitriles, ketones, phosphonates and combinations thereof, having one or more radically transferable groups such as, for example, cyano, cyanato, thiocyanato, azido, halide groups and combinations thereof. Preferably, the radically transferable groups of the monomeric initiator are selected from halide groups (e.g., chloride, bromide and iodide). Additional information can be found, for example, in U.S. Pat. Nos. 5,807,937 and 6,326,420, which are hereby incorporated by reference.

According to a specific embodiment of the invention, an atom transfer radical polymerization process is conducted to provide a polymeric coating on the surface of a medical device. Initially, an alky halide initiator molecule is attached to the medical device surface, to yield, for example,

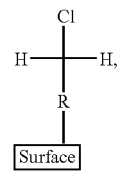

where R is an organic radical, such as a hydrocarbon chain. A transition metal catalyst, such as Cu(I)Cl, and a monomer, such as styrene (as noted above, coordinating monomers such as styrene can be used as a ligand), are introduced to commence chain growth polymerization, which proceeds from the initiator molecule. The result is a medical device with a covalently attached polystyrene coating.

Suitable anionic initiators for use in anionic polymerization embodiments of the present invention include alkyl metal compounds, such as methyl lithium, ethyl lithium, methyl sodium, isopropyl lithium, n-butyl lithium, sec-butyl lithium, tert-butyl lithium, n-dodecyllithium, cyclohexyllithium, 4-cyclohexyllithium butyl sodium, lithium naphthalene, sodium naphthalene, potassium naphthalene, cesium naphthalene, phenyl sodium, phenyl lithium, benzyl lithium, cumyl sodium, cumyl potassium, methyl potassium, ethyl potassium, and so forth.

Cationic initiators for use in cationic polymerization embodiments the present invention are generally of the Lewis acid type, for example, aluminum trichloride, boron trifluoride, boron trifluoride etherate complexes, titanium tetrachloride and the like. If desired, a cationic co-initiator can be added. Suitable cationic co-initiators include tertiary alkyl halides (e.g., t-butylchloride), tert-ester, tert-ether, tert-hydroxyl and tert-halogen containing compounds, such as cumyl esters of hydrocarbon acids, alkyl cumyl ethers, cumyl halides and cumyl hydroxyl compounds and hindered versions of the same. Also, electron pair donors such as dimethyl acetamide, dimethyl sulfoxide, or dimethyl phthalate can be added, as can proton-scavengers that scavenge water, such as 2,6-di-tert-butylpyridine, 4-methyl-2,6-di-tert-butylpyridine, 1,8-bis(dimethylamino)-naphthalene, or diisopropylethyl amine.

In one preferred embodiment, the reaction is commenced by removing a tert-ester, tert-ether, tert-hydroxyl or tert-halogen group from a co-initiator molecule that has been covalently attached to the surface of a medical device by reacting it with the Lewis acid initiator in a suitable solvent system (e.g., a mixture of polar and non-polar solvents such as methyl chloride and hexanes) in the presence of an electron pair donor. In place of the tert-leaving groups is a quasi-stable or "living" cation, which is stabilized by the surrounding tertiary carbons as well as the polar solvent system and electron pair donors. Monomer, such as isobutylene, is introduced, which cationically propagates or polymerizes from each cation on the attached co-initiator molecule. Because the initiator complex is unstable, the monomer (e.g., isobutylene) is commonly added to the reaction before the addition of the Lewis acid initiator (e.g., $TiCl_4$). If desired, an additional monomer such as styrene can subsequently added to form a block copolymer. In this connection, it is noted that a monofunctional initiator produces a diblock copolymer (e.g., polyisobutylene-polystyrene) and a di-functional initiator attached to the surface is used to create a triblock copolymer (e.g., polystyrene-polyisobutylene-polystyrene). The reaction can be terminated by adding a termination molecule such as methanol, water and the like. Further information can be found, for example, in U.S. Pat. Nos. 5,741,331 and 4,946,899, which are hereby incorporated by reference.

In the embodiments discussed above, a polymer coating is provided by attaching one or more species to the surface of a medical device, followed by contact with a monomer, leading to chain-growth polymerization at the site of the attached species. In other embodiments, however, the surface is provided either completely or in part with a catalyst that is used to cause the polymerization reaction at the surface. Subsequently, the medical device exposed to monomer, which then polymerizes in the vicinity of the immobilized catalyst. The catalyst can be immobilized, for example, by covalently bonding it to the surface (including, for example, a coating surface), by physically embedding it in the surface, by plating it onto the surface, by adsorbing it onto the surface, by absorbing it into the surface, and so forth. As the reaction progresses, polymer merges into polymer and thus the integrity of the coating is created by the continuity of the polymer.

For example, the catalyst can be covalently bonded by, for example, treating the surface of the medical device with a reagent that places chemically reactive groups on the device surface or with a coating that supplies such groups. These groups are then reacted with groups that are either inherently found on the catalyst or are supplied to the catalyst (i.e., a derivatized form of the catalyst is used). Covalent attachment of the catalyst may be carried out using numerous known reaction chemistries.

As another example, the surface of the medical device such as a stent can be at least partially covered by a metallic catalyst, for instance, by plating the medical device with a platinum group catalyst. The platinum group metal is subsequently used to catalyze a polymerization reaction, for example, the polymerization of silicone.

The polymerization rates in this embodiment are preferably much greater than the rate at which the formed polymer diffuses away from the surface. Therefore, a polymer is formed that is not covalently attached to the surface of the device, but is concentrated at that surface.

In some embodiments, crosslinking is used to change the properties of the resulting polymer coating. Crosslinking can also provide stronger interaction with the medical device surface, for example, by improving the ability of the polymer to form a unitary mass that surrounds the medical device. Crosslinking strategies are known in the art and include providing the monomer with functional groups that are crosslinkable, e.g., using a crosslinking agent or via photoreaction.

Where chain-growth polymerization reactions are employed, immobilized catalysts include metallocene catalysts, Ziegler-Natta catalysts, atom transfer radical and polymerization catalysts. Where a multi-component catalyst is used, one component of the system may be immobilized. Numerous preferred chain-growth polymers are listed above.

Where step-growth polymerization reactions (typically condensation polymerization reactions) are employed, preferred monomers include terephthalic acid, butanediol, ethylene glycol, toluene diisocyanate (TDI), diphenylmethane diisocyanate (MDI), polyether polyols, hexamethylene diamine, adipic acid, bis-phenol A, diphenyl carbonate (see, e.g., U.S. Pat. No. 6,323,304, which is hereby incorporated by reference), while preferred catalysts for immobilization include the previously discussed platinum group metals, as well as dibutyl tin dilaurate and stannous octoate.

In some step-growth embodiments, dendrimers can be used, allowing branched polymers to be formed.

In all of the above embodiments, polymerization proceeds upon contact with a liquid that contains the selected monomer, as well any other desired components, such as initiators, co-initiators, catalysts, co-catalysts, electron donors and so forth. However, the liquid preferably does not contain sufficient components to cause initiation not attached to the surface. Instead, polymerization preferably occurs at or near the surface upon interaction with species that are provided at the device surface (e.g., initiator, catalyst, etc.).

The monomer containing liquid also typically includes an appropriate solvent system. However, in certain embodiments, polymerization can also be conducted in the absence of solvent (i.e., via a "neat" or "bulk" polymerization process).

The monomer containing liquid can be applied to the medical device (for example, by spraying or rinsing the medical device with the liquid) or, more preferably, the medical device can be immersed in the monomer containing liquid. In these embodiments, multiple medical devices can be produced concurrently.

The thickness of the coating that is formed on the medical device can be controlled in a number of ways, including limiting the amount of monomer that is present, terminating the reaction after a sufficient coating thickness is a achieved, or separating the medical device from the monomer containing liquid after a sufficient coating is a achieved.

Using the above techniques, a wide variety of polymeric coatings can be created. Polymers include (a) polyalkylenes and derivatives such as polyethylenes, polypropylenes, poly-4-methyl-pen-1-eness, polybutylenes (including polybut-1-enes and polyisobutylenes), and fluorinated polyalkylenes (including polytetrafluoroethylenes); (b) polyvinyl polymers and derivatives, such as polystyrenes, polyvinyl chlorides, polyvinyl pyrrolidones, polyacrylonitriles, polyvinyl alcohols, polyvinyl ethers, polyvinyl pyridines, and polyvinyl acetates; and (d) acrylic acid polymers and derivatives, such as methylacrylate polymers, methyl methacrylate polymers, acrylic acid polymers, methacrylic acid polymers, acrylamide polymers, hydroxyethyl acrylate polymers, hydroxyethyl methacrylate polymers, glyceryl acrylate polymers, glyceryl methacrylate polymers, methacrylamide polymers and ethacrylamide polymers, (e) step-growth polymers such as poly(esters), nylons, poly(urethanes), poly(carbonates), and (f) ring-opening polymerization products, such as poly ($\epsilon$-caprolactone) (e.g., nylon 6), poly(L-lactide), poly(glycolide) and poly(p-dioxanone). Also included are copolymers (e.g., block and random copolymers) of the above, including styrene-butadiene copolymers, acrylonitrile-styrene copolymers, acrylonitrile-butadiene-styrene copolymers, styrene-isobutylene copolymers, ethylene-alpha-olefin copolymers, ethylene-methacrylic acid copolymers, ethylene-acrylic acid copolymers, ethylene-methyl methacrylate copolymers and ethylene-vinyl acetate copolymers, ethylene-tetrafluoroethylene copolymers, anhydride functionalized copolymers, such as styrene-maleic anhydride, methylvinylether-maleic anhydride, ring opening copolymers such as copolymers of poly(glycolides), poly(lactides), poly(caprolactones) and poly(p-dioxanone), copolymers of polyamides and ethers, and copolymers of esters and ethers. Random copolymers can be made, for example, by exposing the medical device to a mixture of monomers, while block copolymers can be made, for example, by sequential exposure to different monomers.

The polymer coatings of the present invention are preferably biocompatible for their intended purpose. This means, for example, that the coatings typically do not lead to severe, long-lived or escalating adverse biological responses (which are distinguished, for instance, from the mild, transient inflammation that accompanies implantation of essentially all foreign objects into a living organism).

After the polymer coating is formed, the medical device may be washed in an appropriate solvent to remove unreacted monomer (as well as any other residual species, including initiators, co-initiators, catalysts, co-catalysts and so forth).

A therapeutic agent is preferably provided within the polymer coating on the medical device surface. In some instances, the therapeutic agent can be provided within the polymer coating concurrently with polymer formation (for example, by including the therapeutic agent in the monomer containing liquid). In other instances, the therapeutic agent is incorporated after polymer formation. For example, the therapeutic agent can be dissolved or dispersed within a liquid medium, and the liquid medium contacted with the polymer coating, for example by applying the liquid to the polymer coating (e.g., by spraying or rinsing) or by immersing at least a portion of the medical device within the liquid.

Where the polymer is covalently attached to the medical device surface, the polymer can be contacted with a solvent that would otherwise dissolve the attached polymer. In this way, the polymer can be solubilized, without being removed from the device surface. For example, such a solvent can be used to remove unreacted monomer and/or other residual species from the polymer coating, with diffusion of species out of the polymer being enhanced by the fact that the polymer is solubilized. Alternatively, a solvent of this type can be used to dissolve/disperse a therapeutic agent, which is then contacted with the coating. Analogous to species removal, diffusion of species (in this case, therapeutic agent) into the polymer coating is increased by solubilizing the polymer. Once the solvent is removed, the therapeutic agent is trapped within the polymer.

Therapeutic agents useful in connection with the present invention include essentially any therapeutic agent that is compatible with the selected polymeric coating (e.g., is not adversely affected by the polymeric coating and can be released from the polymeric coating). Therapeutic agents may be used singly or in combination.

"Therapeutic agents", "pharmaceutically active agents", "pharmaceutically active materials", "drugs" and other related terms may be used interchangeably herein and include genetic therapeutic agents, non-genetic therapeutic agents and cells.

Exemplary non-genetic therapeutic agents include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-mitotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promoters; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; and (o) agents that interfere with endogenous vasoactive mechanisms.

Exemplary genetic therapeutic agents include anti-sense DNA and RNA as well as DNA coding for: (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor $\alpha$ and $\beta$, platelet-derived endothelial growth factor, platelet-derived growth factor, tumor necrosis factor $\alpha$, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors of interest for delivery of genetic therapeutic agents include (a) plasmids, (b) viral vectors such as adenovirus, adenoassociated virus and lentivirus, and (c) non-viral vectors such as lipids, liposomes and cationic lipids.

Cells include cells of human origin (autologous or allogeneic), including stem cells, or from an animal source (xenogeneic), which can be genetically engineered if desired to deliver proteins of interest.

A number of the above therapeutic agents and several others have also been identified as candidates for vascular treatment regimens, for example, as agents targeting restenosis. Such agents are appropriate for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/guanylate cyclase stimulants such as forskolin, as well as adenosine analogs, (d) catecholamine modulators including $\alpha$-antagonists such as prazosin and bunazosine, $\beta$-antagonists such as propranolol and $\alpha/\beta$-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK (D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (6-mercaptopurine), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Several of the above and numerous additional therapeutic agents appropriate for the practice of the present invention are also disclosed in U.S. Pat. No. 5,733,925 assigned to NeoRx Corporation, the entire disclosure of which is incorporated by reference.

A wide range of therapeutic agent loadings can be used in connection with the above polymeric coatings, with the amount of loading being readily determined by those of ordinary skill in the art and ultimately depending upon the condition to be treated, the nature of the therapeutic agent itself, the avenue by which the therapeutic-agent-loaded polymeric coating is administered to the intended subject, and so forth. The loaded polymeric coating will frequently comprise from 1% or less to 70 wt % or more therapeutic agent.

Various aspects of the invention relating to the above enumerated in the following paragraphs:

Aspect 1. A method of providing a medical device with a therapeutic agent-releasing polymer coating comprising:
(a) attaching at least one reactive species to a medical device surface, said reactive species leading to chain growth polymerization in the presence of monomer;
(b) contacting said reactive species with at least one monomer species, thereby forming a polymer coating on the surface of the medical device; and
(c) providing at least one therapeutic agent within said polymer coating.

Aspect 2. The method of Aspect 1, wherein at least one therapeutic agent is incorporated during formation of the polymer coating.

Aspect 3. The method of Aspect 1, wherein at least one therapeutic agent is incorporated after formation of the polymer coating.

Aspect 4. The method of Aspect 1, wherein the medical device is an implantable or insertable medical device.

Aspect 5. The method of Aspect 4, wherein the medical device is a stent.

Aspect 6. An implantable or insertable medical device made by the method of Aspect 1.

Aspect 7. The method of Aspect 1, wherein said at least one monomer species comprises an unsaturated monomer.

Aspect 8. The method of Aspect 1, wherein said polymer is selected from polyalkylenes and derivatives, vinyl polymers and derivatives, acrylic acid polymers and derivatives, and copolymers thereof.

Aspect 9. The method of Aspect 1, wherein said polymer is selected from ethylene vinyl acetate and styrene-isobutylene copolymers.

Aspect 10. The method of Aspect 1, wherein said at least one reactive species comprises a free radical species.

Aspect 11. The method of Aspect 10, wherein the free radical species is provided by a process comprising (a) covalently attaching a free-radical initiator molecule to the surface or (b) covalently attaching a species that acquires a free-radical upon exposure to a free radical initiator molecule.

Aspect 12. The method of Aspect 1, wherein said at least one reactive species comprises a carbanion species.

Aspect 13. The method of Aspect 12, wherein the carbanion species is provided by a process comprising (a) covalently attaching an anionic initiator molecule to the surface or (b) covalently attaching a species that acquires a carbanion upon exposure to an anionic initiator molecule.

Aspect 14. The method of Aspect 1, wherein said at least one reactive species comprises a carbocation species.

Aspect 15. The method of Aspect 14, wherein the carbocation species is provided by a process comprising covalently attaching a species that develops a carbocation upon exposure to a cationic initiator molecule.

Aspect 16. The method of Aspect 1, wherein said at least one reactive species comprise a Ziegler-Natta polymerization complex.

Aspect 17. The method of Aspect 1, wherein said at least one reactive species comprises a metallocene complex.

Aspect 18. The method of Aspect 1, wherein said at least one reactive species comprises an atom transfer radical polymerization initiator.

Aspect 19. The method of Aspect 18, wherein the at least one reactive species is provided by a process comprising (a) covalently attaching an atom transfer radical polymerization initiator molecule to the surface or (b) covalently attaching a species that acquires a free-radical upon exposure to an atom transfer radical polymerization initiator and an atom transfer radical polymerization catalyst.

Aspect 20. The method of Aspect 1, wherein the at least one reactive species is formed from a derivatized monomer that is covalently bonded to the surface of the medical device.

Aspect 21. The method of Aspect 1, wherein the at least one reactive species is formed from a derivatized initiator compound that is covalently bonded to the surface of the medical device.

Aspect 22. A method of providing a medical device with a therapeutic agent-releasing coating comprising:
(d) immobilizing least one polymerization catalyst at a medical device surface, said polymerization catalyst leading to polymerization in the presence of monomer;
(e) contacting the medical device surface with at least one monomer species, thereby forming a polymer coating at the medical device surface; and
(f) providing at least one therapeutic agent within said polymer coating.

Aspect 23. The method of Aspect 22, wherein the at least one polymerization catalyst is immobilized by covalently bonding it to said surface.

Aspect 24. The method of Aspect 22, wherein the at least one polymerization catalyst is immobilized by physically embedding it in said surface.

Aspect 25. The method of Aspect 22, wherein the medical device surface is at least partially covered by a metal catalyst.

Aspect 26. The method of Aspect 22, further comprising cross-linking said polymer coating.

Aspect 27. The method of Aspect 22, wherein the at least one monomer species comprises a dendrimer.

Aspect 28. The method of Aspect 22, wherein at least one therapeutic agent is provided within the polymer coating during formation of the polymer coating.

Aspect 29. The method of Aspect 22, wherein at least one therapeutic agent is provided within the polymer coating after formation of the polymer coating.

Aspect 30. The method of Aspect 22, wherein the medical device is an implantable or insertable medical device.

Aspect 31. The method of Aspect 30, wherein the medical device is a stent.

Aspect 32. An implantable or insertable medical device made by the method of Aspect 22.

Aspect 33. The method of Aspect 22, wherein said polymer is selected from ethylene vinyl acetate copolymers, poly(ε-caprolactone), styrene-isobutylene copolymers and silicone.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A method of providing a medical device with a therapeutic agent-releasing polymer coating comprising:
(a) covalently attaching an atom transfer radical polymerization initiator molecule to a medical device surface;
(b) contacting said initiator molecule with at least one monomer species in the presence of an atom transfer radical polymerization catalyst, thereby forming a polymer coating on the surface of the medical device;
(c) providing at least one therapeutic agent within said polymer coating; and
(d) cross-linking said polymer coating.

2. The method of claim 1, wherein at least one therapeutic agent is incorporated during formation of the polymer coating.

3. The method of claim 1, wherein at least one therapeutic agent is incorporated after formation of the polymer coating.

4. The method of claim 1, wherein the medical device is an implantable or insertable medical device.

5. The method of claim 4, wherein the medical device is a stent.

6. The method of claim 1, wherein said at least one monomer species comprises an unsaturated monomer.

7. The method of claim 1, wherein said polymer is selected from the group consisting of polyalkylenes and derivatives, vinyl polymers and derivatives, acrylic acid polymers and derivatives, and copolymers thereof.

8. The method of claim 1, wherein said polymer is selected from the group consisting of ethylene vinyl acetate and styrene-isobutylene copolymers.

9. A method of providing a medical device with a therapeutic agent-releasing coating comprising:
(a) immobilizing at least one polymerization catalyst at a medical device surface, said polymerization catalyst leading to polymerization in the presence of monomer;
(b) contacting the medical device surface with at least one monomer species, thereby forming a polymer coating at the medical device surface;
(c) providing at least one therapeutic agent within said polymer coating; and
(d) cross-linking said polymer coating.

10. The method of claim 9, wherein the at least one polymerization catalyst is immobilized by covalently bonding it to said surface.

11. The method of claim 9, wherein the medical device surface is at least partially covered by a metal catalyst.

12. The method of claim 9, wherein at least one therapeutic agent is provided within the polymer coating during formation of the polymer coating.

13. The method of claim 9, wherein at least one therapeutic agent is provided within the polymer coating after formation of the polymer coating.

14. The method of claim 9, wherein the medical device is an implantable or insertable medical device.

15. The method of claim 14, wherein the medical device is a stent.

16. The method of claim 9, wherein said polymer is selected from the group consisting of ethylene vinyl acetate copolymers, poly(ε-caprolactone), styrene-isobutylene copolymers and silicone.

17. A method of providing a medical device with a therapeutic agent-releasing coating comprising:
(a) immobilizing at least one polymerization catalyst at a medical device surface by physically embedding said polymerization catalyst in said surface, said polymerization catalyst leading to polymerization in the presence of monomer;
(b) contacting the medical device surface with at least one monomer species, thereby forming a polymer coating at the medical device surface; and
(c) providing at least one therapeutic agent within said polymer coating.

18. A method of providing a medical device with a therapeutic agent-releasing coating comprising:

(a) immobilizing at least one polymerization catalyst at a medical device surface, said polymerization catalyst leading to polymerization in the presence of monomer;
(b) contacting the medical device surface with at least one monomer species, thereby forming a polymer coating at the medical device surface, wherein the at least one monomer species comprises a dendrimer; and
(c) providing at least one therapeutic agent within said polymer coating.

* * * * *